United States Patent [19]

Lee

[11] 4,140,489
[45] Feb. 20, 1979

[54] TEST TUBE FOR EASY ENUMERATION AND CULTIVATION OF ANAEROBIC AND FACULTATIVELY ANAEROBIC MICROORGANISMS

[76] Inventor: Sun Y. Lee, 5608 Orion Cir., Golden, Colo. 80401

[21] Appl. No.: 766,220

[22] Filed: Feb. 7, 1977

[51] Int. Cl.² .......................... B65D 1/04; C12B 1/02; G01N 1/10
[52] U.S. Cl. ............................. 195/103.5 R; 195/127; 356/246; 215/6
[58] Field of Search .................. 23/259, 292; 195/127; 356/246; 215/1 R, 6

[56] References Cited

U.S. PATENT DOCUMENTS

| | | | |
|---|---|---|---|
| 2,470,806 | 5/1949 | Del Cueto | 215/1 R X |
| 2,587,221 | 2/1952 | Richardson et al. | 23/292 X |
| 3,481,712 | 12/1969 | Bernstein et al. | 23/259 X |
| 3,627,432 | 12/1971 | Bergmann | 23/292 X |
| 3,807,955 | 4/1974 | Note, Jr. et al. | 23/292 X |

OTHER PUBLICATIONS

Aloe Scientific, Catalog 103, 1952, p. 424.

*Primary Examiner*—Robert M. Reese
*Attorney, Agent, or Firm*—Kyle W. Rost

[57] ABSTRACT

A test tube having an inner tube that allows one to insert a bar to create a dark background is described. This system is actually an ordinary or screw-capped test tube with a smaller sized test tube inverted and fused to the bottom. The design permits a thin layer of any agar medium to solidify around the inside edge of the larger tube. The colonies developed in the agar can then be easily counted by creating a dark background by inserting a dark colored rod through the opening of the inner tube.

Alternatively, a permanently dark-colored inner tube can be inverted and fused to the bottom of the outer tube. In this case, it is not necessary to insert a rod to create a dark background and the enumeration of microbial colonies is as easy as the method described above.

2 Claims, 4 Drawing Figures

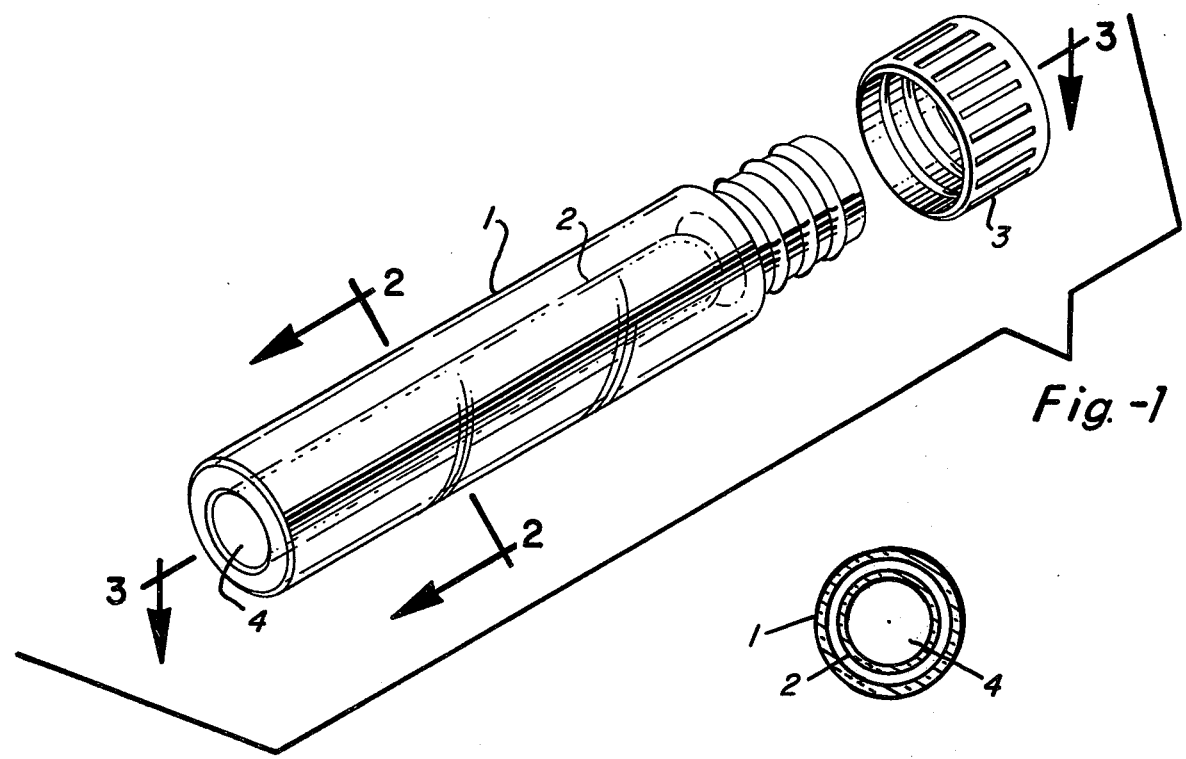
Fig.-1
Fig.-2
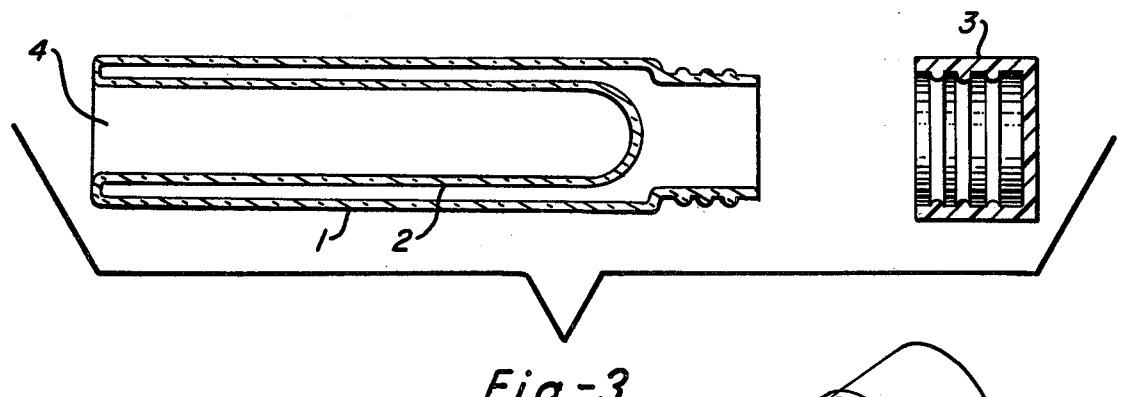
Fig.-3
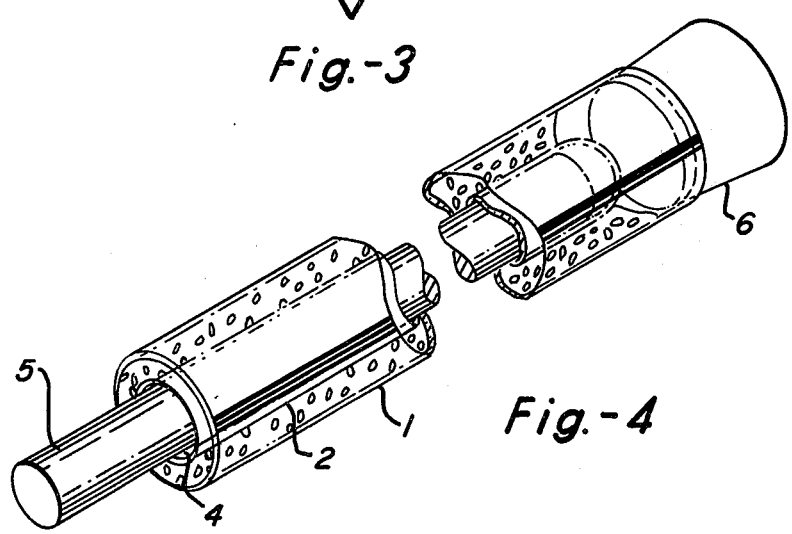
Fig.-4

TEST TUBE FOR EASY ENUMERATION AND CULTIVATION OF ANAEROBIC AND FACULTATIVELY ANAEROBIC MICROORGANISMS

BACKGROUND OF THE INVENTION

1. Field of the Invention

The invention relates to test tubes used in the microbiological field. More specifically, the invention is a test tube having a smaller test tube inverted and fused to the bottom (hereafter referred to as Lee's Tube). This design permits a layer of agar medium to solidify around the inside edge of the outer tube with a minimal incorporation of oxygen. At the same time, a black wooden or plastic rod may be inserted into the smaller tube to provide a dark background for easier counting. On the other hand, a permanently dark colored inner tube can be inverted and fused to the bottom of the outer tube. This will create the same dark-background effect without inserting a colored rod.

A rubber stopper or screw cap can be used for closing the tube. In this system, anaerobic, or facultatively anaerobic microorganisms will grow well while the ordinary petri plate fails to provide the same results. The tube saves space in the incubator and can even be incubated in a water bath for faster cultivation of test organisms. It is also suitable to carry in the field where petri plates give difficulties in handling.

2. Description of the Prior Art

The methods of cultivation or enumeration of a given microbiological sample are rather unique. The most popular method presently used is the petri plate. The petri plate consists of a bottom and a cover. The sample is properly diluted and delivered to the bottom of the dish. Molten agar is then added and allowed to solidify. Since the structure of the petri plate is as such, a large amount of oxygen is incorporated into the medium during processing of the sample, causing the inhibition of anaerobic or facultatively anaerobic microorganisms. To overcome this problem, the petri plate is simply incubated in an incubator containing $CO_2$, $N_2$, $H_2$ or combinations of these gases. But this is an expensive, time-consuming operation which needs special equipment with a well-trained technician. The other technique for the cultivation of anaerobic bacteria employs the use of a pre-reduced medium in an ordinary test tube. In this method, a pre-reduced medium in a tube with a rubber stopper is autoclaved and cooled in a water bath. The test sample is then inoculated under the $CO_2$ or $N_2$ stream followed by spinning the tube horizontally. After the agar and the sample mixture have been solidified, the tube is incubated. Here again, the procedure is complicated, time-consuming, and requires the services of a highly trained microbiologist.

Even after the anaerobes have grown in the tube, it is very difficult to enumerate the developed colonies because the colonies on the other side of the agar surface are visible through the transparent glass tube.

The present invention allows one to overcome all these problems. The method of cultivating microorganisms is as simple as in the petri plate method and yet it provides a complete blockage of the view of the other side of the tube. Therefore, counting is as easy as in the petri plate method. Strict anaerobes can be grown by employing the rubber stopper and a proper anaerobic technique.

SUMMARY OF THE INVENTION

A test tube having an inner tube that allows one to insert a bar to create a dark background is described. This system is actually an ordinary or screw-capped test tube with a smaller sized test tube inverted and fused to the bottom. The design permits a thin layer of any agar medium to solidify around the inside edge of the larger tube. The colonies developed in the agar can then be easily counted by creating a dark background by inserting a dark colored rod through the opening of the inner tube.

Alternatively, a permanently dark-colored inner tube can be inverted and fused to the bottom of the outer tube. In this case, it is not necessary to insert a rod to create a dark background and the enumeration of microbial colonies is as easy as the method described above.

A test tube having an inner tube that is inverted and fused to the bottom of the outer tube is described. The tube can be constructed either with glass or varieties of clear plastic materials. The mouth of the tube is either plain or screwed so that a rubber stopper or a screw cap can be used for closing the tube.

One object of the invention is to create a dark background on the inside of the tube so one can easily count the colonies developed in the tube without confusion. A black or dark-colored rod can be inserted from the bottom of the tube for a complete blockage of the other side of the tube surface. Alternatively, a permanently dark colored inner tube can be substituted. In this case, the insertion of a dark rod is not necessary.

Another important object is to decrease the oxygen content to provide an environment suitable for the cultivation of anaerobic and facultatively anaerobic microorganisms. Aerobic microorganisms can also be cultivated in this tube by simply skipping the anaerobic technique and incubating with a loosened screw cap.

Still another important object is to provide a simple device for enumeration of anaerobic and facultatively anaerobic microorganisms. This will eliminate the expensive and complicated techniques. This tube can even be incubated in a water bath where a more even temperature is expected. This will stimulate the growth of test organisms more than at regular incubator with air. It is space saving and lessens the chance of contamination of the sample because of the smaller opening.

BRIEF DESCRIPTION OF THE DRAWINGS

FIG. 1 is a perspective view of the invention where the outer tube, inner tube, and the hole for insertion of a bar is shown. A screw cap is used here for closing the tube.

FIG. 2 is a vertical cross section of the invention taken along the plane of line 2—2 of FIG. 1.

FIG. 3 is a horizontal cross section of the invention taken along the plane of line 3—3 of FIG. 1.

FIG. 4 exhibits the bacterial colony formation in the solid medium and also the inserted black bar, to enhance the counting efficiency of the developed bacterial isolates. A rubber stopper is used here to close the tube.

DESCRIPTION OF THE PREFERRED MATERIALS FOR THE CONSTRUCTION OF THE LEE'S TUBE

As shown in the drawings, microorganisms are grown in a test tube 1, having an inner tube, 2, that enables one to insert a bar, 5, to create a dark background for easy quantitation. A variety of construction materials can be used for the test tube and the size of the tube (inner as well as outer) can also be varied depending upon test purposes. Basically, the test tube can be constructed with clear glass for repeated use. The screw cap, 3, which is used for closing purposes in the tube can be replaced by a rubber stopper, 6, for the cultivation of strict anaerobic microorganisms. On the other hand, biologically inert, clear, opaque, or translucent plastics are also excellent materials for the construction. For example, polycarbonate is clear, very tough, inert, and resistant to high temperature and is therefore suitable for the construction of Lee's Tube. Other plastics that can be used for the construction of Lee's Tube are polystyrene (styrene), high impact polystyrene, styrene acrylonitrile, polyethylene (high density), polyethylene (low density), polypropylene, methyl methacrylate, cellulose acetate, nylon, P.T.E. (Teflon), P.V.C. (plasticized), vinyl-chloride, cellulose nitrate, and polypropylene.

Alternatively, the inner tube, 2, can be initially dark colored. This will eliminate the use of a bar for insertion. When a dark colored inner tube is used, either the opening of the inner tube, 4, is completely sealed or left open.

With reference to FIGS. 2 and 3, the outer tube 1 and the inner tube 2 are concentric and form an annular area therebetween for the length of the inner tube, which area contains growth medium for microbial colonies, as shown in FIG. 4. Inner tube 2 forms an internal longitudinally extending passageway adapted to receive background medium such as rod 5 therein.

Tubes 1 and 2 have first and second ends in respectively corresponding directions, the first end of the outer tube forming an opening for receiving growth medium and microbial organisms to be cultivated therein. Cap means such as stopper 6 or screw cap 3 are engageable with the first end of the outer tube 1 to seal the opening. The second ends of tubes 1 and 2 are joined by an end wall to close the annular area between the tubes at this end. However, the second end of the inner tube 2 remains centrally open at 4 to receive the background medium into the longitudinal passageway. The first end of the inner tube is centrally closed by sealing means such as a wall, as illustrated in FIG. 3, spaced inwardly from the open first end of the outer tube.

I claim:

1. The method of cultivating and enumerating anaerobic and facultatively anaerobic microorganisms, comprising:

(a) cultivating microorganisms in an agar medium in a culture tube having concentric inner and outer tube walls forming an annular area therebetween and containing said agar, wherein the tube walls have first and second ends in corresponding directions, the first end of the outer tube wall forming an opening for receiving the agar and microorganisms and having sealing means closing the first end during cultivation, the second end of the outer tube wall being connected to the second end of the inner tube wall, the first end of the inner tube wall being sealed and spaced inwardly from the first end of the outer tube wall, and the second end of the inner tube wall being open and having an internal longitudinal passageway extending to the sealed first end thereof;

(b) inserting colored background medium into said longitudinal passageway of the inner tube wall; and (c) enumerating the cultivated microorganisms against said background.

2. A device for enumeration and cultivation of microbial colonies comprising, in combination:

(a) a test tube-like tube having (1) inner and outer concentric tube walls forming an annular area therebetween for containing growth medium for the microbial colonies, the inner wall forming an internal longitudinally extending passageway for receiving background medium therein, the inner and outer tube walls having first and second longitudinal ends in respectively corresponding directions, the first end of the outer tube wall forming an opening for receiving growth medium and microbial organisms to be cultivated therein, wherein the diameter of the mouth is substantially greater than the distance between the inner and outer tube walls and the distance between said inner and outer tube walls is narrower than the diameter of said passageway;

(2) an end wall joining the second end of the outer wall and the second end of the inner wall for sealing the annular area between the outer and inner walls at the second ends of the tube walls, the second end of the inner tube wall forming an opening into said passageway, the outer tube wall being of transparent material for allowing enumeration of microbial colonies in the annular area; and (3) sealing means closing the first end of the inner tube wall;

(b) cap means engageable with said opening in the first end of the outer tube wall for sealing said opening; and (c) colored background medium insertable into said passageway through said second end of the inner tube wall.

* * * * *